US008260411B1

(12) United States Patent
Odland et al.

(10) Patent No.: US 8,260,411 B1
(45) Date of Patent: Sep. 4, 2012

(54) CONDUCTIVE INJECTION AND ASPIRATION DEVICE AND METHOD

(75) Inventors: Rick Mathew Odland, Roseville, MN (US); Bradford G. Staehle, Minnetonka, MN (US); Scott R. Wilson, Maple Grove, MN (US)

(73) Assignee: Twin Star Medical, Inc., Minneapolis, MN (US)

( * ) Notice: Subject to any disclaimer, the term of this patent is extended or adjusted under 35 U.S.C. 154(b) by 658 days.

(21) Appl. No.: 11/516,447

(22) Filed: Sep. 6, 2006

(51) Int. Cl.
*A61N 1/30* (2006.01)
(52) U.S. Cl. ............... 604/21; 604/20; 604/27; 606/41
(58) Field of Classification Search .............. 604/19–21, 604/93.01, 103.01, 102.01, 509, 27; 606/41
See application file for complete search history.

(56) References Cited

U.S. PATENT DOCUMENTS

| 5,213,576 | A | * | 5/1993 | Abiuso et al. ........... 604/103.01 |
| 5,286,254 | A | | 2/1994 | Shapland et al. ............... 604/21 |
| 5,441,481 | A | | 8/1995 | Mishra et al. .................. 604/29 |
| 5,472,441 | A | * | 12/1995 | Edwards et al. ................ 606/41 |
| 5,554,110 | A | * | 9/1996 | Edwards et al. ................ 604/22 |
| 5,669,874 | A | * | 9/1997 | Feiring ............................ 604/21 |
| 5,865,787 | A | | 2/1999 | Shapland et al. ............... 604/21 |
| 6,026,316 | A | | 2/2000 | Kucharczyk et al. ......... 600/420 |
| 6,032,077 | A | * | 2/2000 | Pomeranz .................... 607/101 |
| 6,893,429 | B2 | | 5/2005 | Petersen ...................... 604/537 |
| 6,958,060 | B2 | | 10/2005 | Mathiesen et al. ............ 604/511 |
| 6,978,172 | B2 | | 12/2005 | Mori et al. .................... 604/20 |
| 2003/0060822 | A1 | * | 3/2003 | Schaer et al. .................. 606/41 |
| 2007/0213686 | A1 | * | 9/2007 | Mathur et al. ................ 604/518 |
| 2008/0132826 | A1 | * | 6/2008 | Shadduck et al. ............. 604/24 |

OTHER PUBLICATIONS

Concentric. Merriam-Webster Online Dictionary. 2009. Merriam-Webster Online. Dec. 10, 2009 http://www.merriam-webster.com/dictionary/concentric.*

* cited by examiner

*Primary Examiner* — Kevin C Sirmons
*Assistant Examiner* — Emily Schmidt
(74) *Attorney, Agent, or Firm* — Fredrikson & Byron, PA

(57) ABSTRACT

A medical device having incorporated electrodes that can be used for delivering drugs or other therapeutic fluids at a uniform rate over an extended area to an internal anatomical location of a patient's body. The device can also be used for aspirating excess fluid from an internal anatomical location of a patient's body.

17 Claims, 13 Drawing Sheets

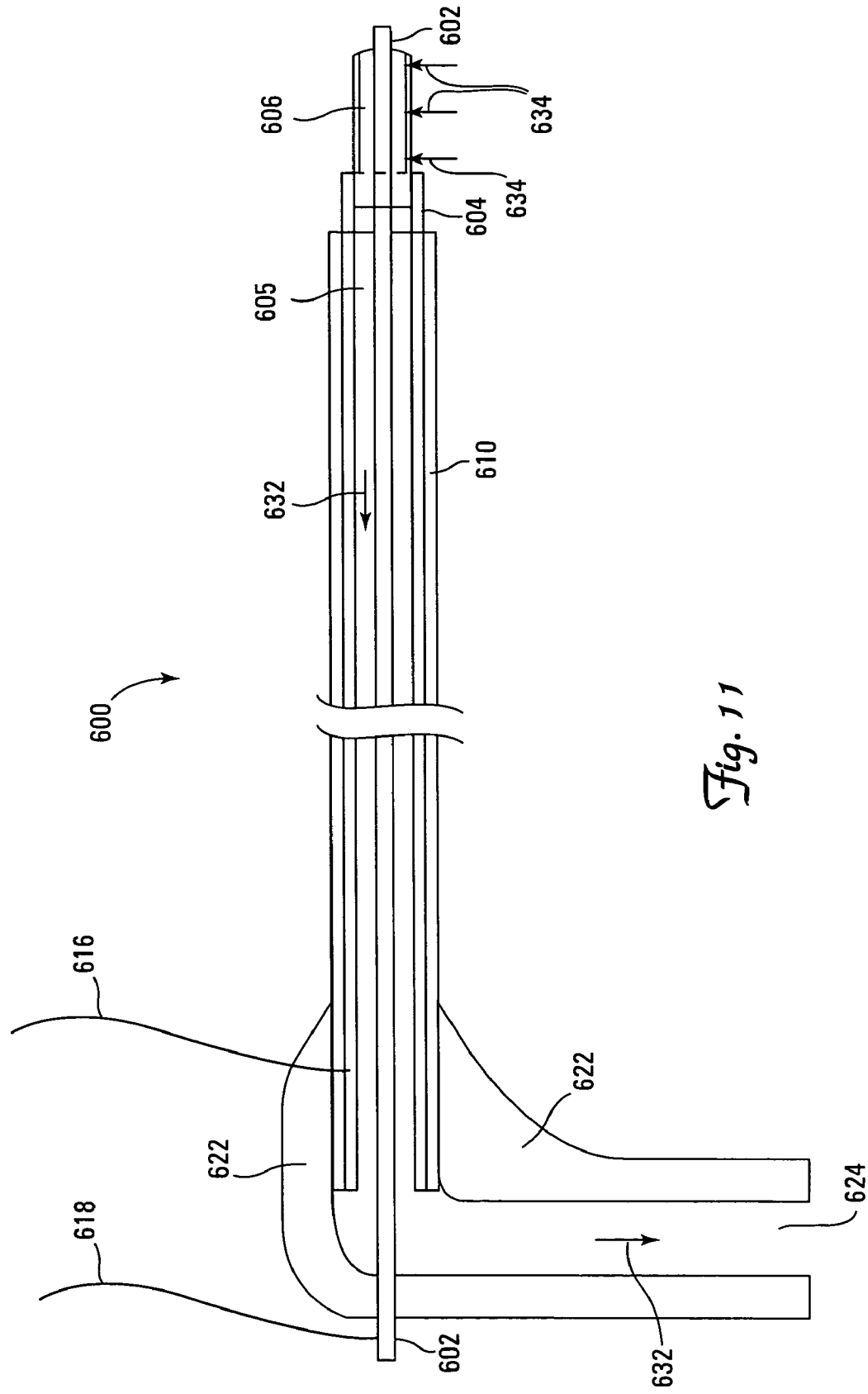

CONDUCTIVE INJECTION AND ASPIRATION DEVICE AND METHOD

FIELD OF THE INVENTION

The invention relates to devices used to inject and or aspirate therapeutic and/or biological fluids generally and more specifically to devices capable of conducting an electrical signal to the area to be treated to increase cellular uptake of a therapeutic fluid injected by the device.

BACKGROUND

Electroporation, which is also known as electropermeabilization, involves a significant increase in electrical conductivity and permeability of the cell plasma semi-permeable membrane which is caused by applying an electric field to an area of a patient's body desired to be treated. Ordinarily, electroporation is used in molecular biology to introduce a substance inside the cell, such as loading it with a molecular probe, a drug that can change the cell's function or a piece of coding DNA. An unnatural increase in permeability is usually explained as a process of formation of very small openings (pores) in the plasma membrane, which increases the body's ability to absorb the therapeutic agent. If the strength of the electrical field and duration of exposure to it are properly chosen, the pores formed by the electrical pulse reseal after a short period of time, during which the extracellular compounds are better able to get inside the cell. A device that would evenly distribute a drug or therapeutic fluid to a specific internal anatomical location within a patient's body at a controlled rate that could also accurately apply an electric field to increase the permeability of the intended tissue would be extremely desirable.

Hollow fibers are made from porous polymers that were developed to improve the distribution of drugs administered directly into the central nervous system. It has been found that using a porous polymer hollow fiber significantly increases the surface area of brain tissue that the drug or therapeutic fluid is infused into. Dye was infused into a mouse brain by convection-enhanced delivery using a 28 gauge needle compared to a hollow fiber having a 3 mm length. Hollow fiber mediated infusion increased the volume of brain tissue labeled with dye by a factor of 2.7 times compared to using a conventional needle. In order to determine if hollow fiber use could increase the distribution of gene therapy vectors, a recombinant adenovirus expressing the firefly luciferase reporter was injected into the mouse striatum. Gene expression was monitored using in vivo luminescent imaging. In vivo imaging revealed that hollow fiber mediated infusion of adenovirus resulting in gene expression that was an order of magnitude greater than when a conventional needle was used for delivery. To assess distribution of gene transfer, an adenovirus expression green fluorescent protein was injected into the striatum using a hollow fiber and a conventional needle. The hollow fiber greatly increased the area of brain transduced with adenovirus relative to a needle, transducing a significant portion of the injected hemisphere.

SUMMARY

In one aspect, the invention includes a catheter having a first conductive member. A second conductive member defines a length and a lumen capable of transporting fluids along the length of the second conductive member. A semi-permeable membrane is attached to the second conductive member to regulate fluid passage through the second conductive member and a fitting is attached to the catheter which allows fluid communication with the lumen.

In another aspect, the invention includes a catheter having a proximal section which extends distally from a fitting to a point proximal of an external electrical contact section. The external electrical contact section extends distally from a distal end of the proximal section to the proximal end of a semi-permeable membrane section and the semi-permeable membrane section extends distally from a distal end of the external electrical contact section to a proximal end of a distal section. The distal section extends distally from a distal end of the semi-permeable membrane section to a distal end of the catheter. A first electrically conducting hollow member defines an outer dimension, a lumen and a distal end with at least one opening through the first hollow member allowing fluid communication between the lumen and an outer surface of the first hollow member. A first insulator encases the first hollow member and extends longitudinally over the proximal section, the external electrical contact section and the semi-permeable membrane section. A second electrically conducting hollow member defines an inner dimension sufficiently large to surround the outer dimension of the first hollow member, surrounding the first hollow member. The proximal section of the second hollow member is encased by a second insulator. A semi-permeable membrane is attached to the outer surface of the first hollow member and extends from the distal end of the external electrical contact section to a proximal end of the distal section and covers the at least one opening. The semi-permeable membrane defines a pore structure allowing fluid communication between the lumen and an area outside the semi-permeable membrane.

In an alternative aspect, the invention includes a catheter having an electrically conducting outer member defining a length and defining a lumen capable of transporting fluids along the length. The outer member is insulated except for an exposed portion capable of functioning as an electrode. A hollow, semi-permeable membrane is attached at a first point to the outer member which allows fluid to pass through the semi-permeable membrane. An electrically conducting central member is surrounded by and sealed to the outer member and does not contact the outer member. At least the portion of the central member surrounded by the outer member and semi-permeable member is insulated. A portion of the central member extends from the semi-permeable membrane and functions as an electrode. A fixture is attached at a second point to the outer member and allows fluid communication with the lumen. The semi-permeable membrane forms a fluid collection chamber allowing fluid passage through the semi-permeable member.

In yet another aspect, the invention includes a method of in vivo administration of a therapeutic fluid. The method includes the steps of: (1) Introducing into a patient a catheter defining a lumen allowing fluid communication through the lumen, which has an incorporated first electrode and an incorporated second electrode and a semi-permeable membrane allowing pressurized fluid to exit the lumen. (2) Adjusting the position of the catheter thereby determining correct placement of the catheter. (3) Attaching a fluid containing pressure generating device to the catheter. (4) Applying positive fluid pressure to the lumen causing the fluid to exit the lumen through the semi-permeable membrane. (5) Impressing an electric signal on the second electrode to increase permeability of the plasma membrane at the anatomical location proximate the area of the exposed first and second electrodes of the introduced catheter.

In still another aspect, the invention includes a method of aspirating fluid from a patient. The method includes the steps of: (1) Introducing into a patient a catheter defining a lumen allowing fluid communication through the lumen, which has an incorporated first electrode and an incorporated second electrode and a semi-permeable membrane allowing fluid to exit the lumen. (2) Adjusting the position of the catheter thereby determining correct placement of the catheter. (3) Attaching a vacuum generating device to the catheter. (4) Applying negative fluid pressure to the lumen causing fluid surrounding the introduced catheter to enter the lumen through the semi-permeable membrane. (5) Impressing an electric signal on the second electrode to increase permeability of the plasma membrane at the anatomical location proximate the area of the exposed first and second electrodes of the introduced catheter. (6) Withdrawing fluid from the patient.

BRIEF DESCRIPTION OF THE DRAWINGS

FIG. 11 is a cross sectional centerline view taken through the longitudinal axis of an embodiment of the injection/aspiration device shown in FIGS. 8-10, showing fluid from a patient passing through the semi-permeable membrane into the fluid collection chamber, resulting from negative pressure applied to the lumen.

DETAILED DESCRIPTION

Figure 1:
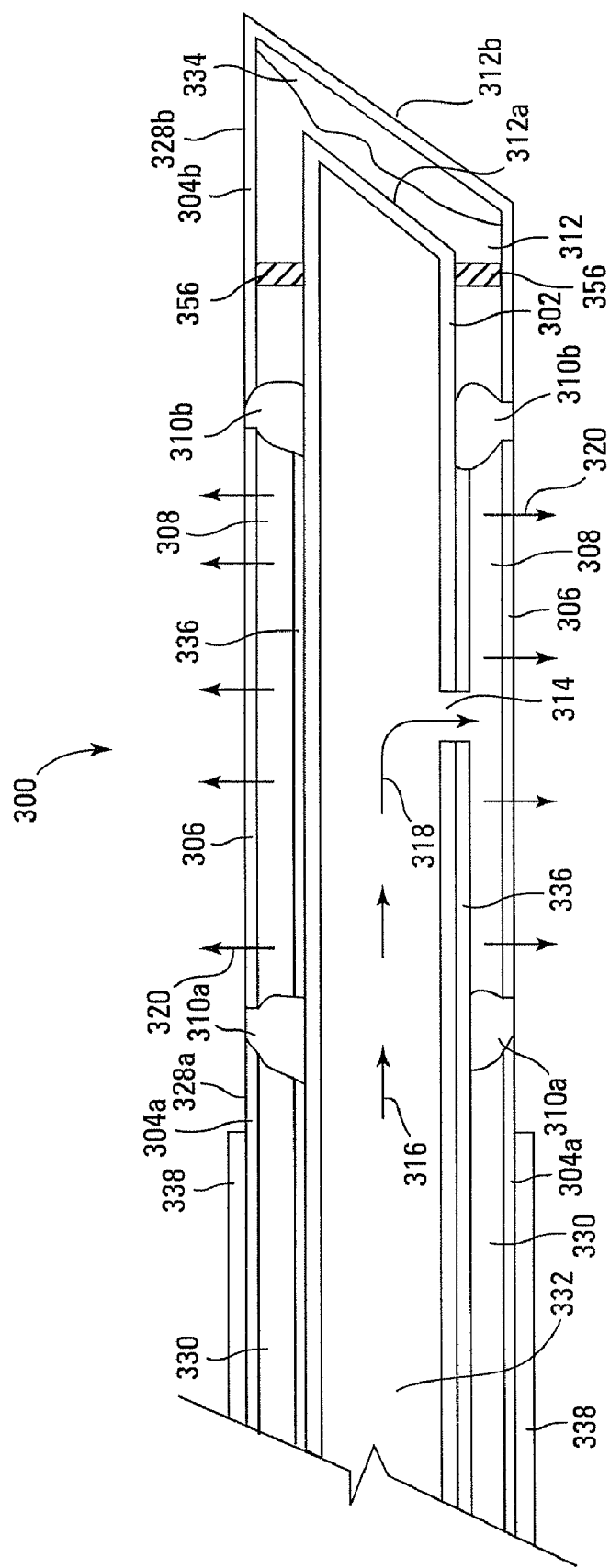
FIG. 1 is a cross sectional centerline view taken along the longitudinal axis of an embodiment of the injection/aspiration device having incorporated insulated metallic elements also functioning as electrodes, showing fluid passing through the semi-permeable membrane resulting from positive pressure applied to the lumen.

The particulars shown herein are by way of example and for purposes of illustrative discussion of the invention only and are presented in the cause of providing what is believed to be the most useful and readily understood description of the principles and conceptual aspects of the invention. In this regard, no attempt is made to show structural details of the invention in more detail than is necessary for the fundamental understanding of the invention, the description taken with the drawings making apparent to those skilled in the art how the several forms of the invention may be embodied in practice.

NOMENCLATURE

| | |
|---|---|
| 40 | Syringe |
| 300 | Injection/Aspiration Device |
| 302 | First Hollow Member |
| 304a | Second Hollow Member (Proximal Section) |
| 304b | Second Hollow Member (Distal Section) |
| 306 | Semi-Permeable Membrane |
| 308 | Fluid Collection Chamber |
| 310a | Bonding Agent (Proximal Layer) |
| 310b | Bonding Agent (Distal Layer) |
| 312a | Distal End of First Hollow Member |
| 312b | Distal End of Second Hollow Member (Distal Section) |
| 314 | Opening |
| 316 | Arrow Depicting Positive Fluid Pressure |
| 318 | Arrow Depicting Fluid Passing Through Opening |
| 320 | Arrow Depicting Fluid Passing Through Semi-Permeable Membrane to Patient |
| 322 | Arrow Depicting Negative Pressure in Lumen |
| 324 | Arrow Depicting Fluid Passing Through Opening Into Lumen |
| 326 | Arrow Depicting Fluid Passing Through Semi-Permeable Membrane Into Fluid Collection Chamber |
| 328a | Outer Surface of Proximal Section of Second Hollow Member |
| 328b | Outer Surface of Distal Section of Second Hollow Member |
| 330 | Second Lumen |
| 332 | First Lumen |
| 334 | Plug |
| 336 | First Insulator |
| 338 | Second Insulator |
| 340 | Fitting |
| 342 | First Electrical Lead |
| 344 | Second Electrical Lead |
| 346 | Proximal Section |
| 348 | External Electrical Contact Section |
| 350 | Semi-Permeable Membrane Section |
| 352 | Distal Section |
| 354 | Power Source |
| 356 | Conductive Material |
| 500 | Injection/Aspiration Device |
| 502 | First Hollow Member |
| 504a | Second Hollow Member (Proximal Section) |
| 504b | Second Hollow Member (Distal Section) |
| 506 | Semi-Permeable Membrane |
| 508 | Fluid Collection Chamber |
| 510a | Bonding Agent (Proximal Layer) |
| 510b | Bonding Agent (Distal Layer) |
| 512a | Distal End of First Hollow Member |
| 512b | Distal End of Second Hollow Member (Distal Section) |
| 514 | Opening |
| 528a | Outer Surface of Proximal Section of Second Hollow Member |
| 528b | Outer Surface of Distal Section of Second Hollow Member |
| 530 | Second Lumen |
| 532 | First Lumen |
| 534 | Plug |
| 536 | First Insulator |
| 538 | Second Insulator |
| 540 | Fitting |
| 542 | First Electrical Lead |
| 544 | Second Electrical Lead |
| 546 | Proximal Section |
| 548 | External Electrical Contact Section |
| 550 | Semi-Permeable Membrane Section |
| 552 | Distal Section |
| 554 | Power Source |
| 556 | Conductive Material |
| 600 | Injection/Aspiration Device |
| 602 | Solid Member |

-continued

| | | |
|---|---|---|
| 602a | Proximal End of Solid Member | |
| 602b | Distal End of Solid Member | |
| 604 | Hollow Member | |
| 604b | Distal End of Hollow Member | |
| 604c | Distal Termination of Hollow member | |
| 605 | Lumen of Hollow Member | |
| 606 | Semi-Permeable Membrane | |
| 608 | First Insulator | |
| 610 | Second Insulator | |
| 612 | Proximal Layer of Bonding Agent | |
| 614 | Distal Layer of Bonding Agent | |
| 616 | First Electrical Lead | |
| 618 | Second Electrical Lead | |
| 620 | Power Source | |
| 622 | Fitting | |
| 624 | Fluid Channel | |
| 626 | Fluid Collection Chamber | |
| 628 | Arrow Depicting Positive Fluid Pressure | |
| 630 | Arrow Depicting Fluid Passing Through Semi-Permeable Membrane to Patient | |
| 632 | Arrow Depicting Negative Pressure | |
| 634 | Arrow Depicting Fluid Passing Through Semi-Permeable Membrane Into Fluid Collection Chamber | |

DEFINITIONS

"Catheter" is used in its general sense and refers to a conduit capable of transporting a substance, fluid or an electrical signal to a remote location.

"Distal" means further from the point controlled by the operator (e.g., physician or technician) of a device.

"Electrode" means an exposed conductor allowing electrical communication between a conductive structure or substance and the electrode.

"Fluid" means a substance offering no permanent resistance to change of shape, such as a gas or a liquid.

"Hollow Member" means a structure having an outer surface and a hollow space enclosed by the outer surface.

"Proximal" means closer to the point controlled by the operator (e.g., physician or technician) of a device.

"PTFE" means polytetrafluoroethylene.

"Semi-Permeable Membrane" means a porous or semi-permeable barrier permitting controlled fluid passage under certain conditions.

"Weep" means the controlled flow of fluid through a membrane.

Construction

Electroporation or electropermeabilization requires a significant increase in the electrical conductivity and permeability of lipid bilayer semi-permeable plasma or cell membranes caused by applying electric field pulses at specified intervals. The unnatural increase in permeability is theoretically explained as a process of formation of very small openings (pores) in a cell (plasma) membrane. If the strength of the electrical field and duration of exposure to it are properly chosen, the pores formed by the electric pulse are open for a short period of time, during which extracellular compounds have a chance to permeate the cell. After a short period of time the pores reseal. One of the advantages to using electroporation in a drug or therapeutic fluid delivery application is that following the introduction of the electrical field, when the formed pores are open, the drug or therapeutic fluid is taken up by the effected cells more rapidly. The result of this is that a smaller volume or concentration of the drug or therapeutic fluid is required to achieve a similar outcome as would be required without electroporation, which decreases potential toxicity to the patient. An additional advantage to electroporation is that it is possible to more specifically target particular affected anatomical areas, again resulting in treatment using a smaller volume or concentration to achieve the same outcome.

Figure 2:
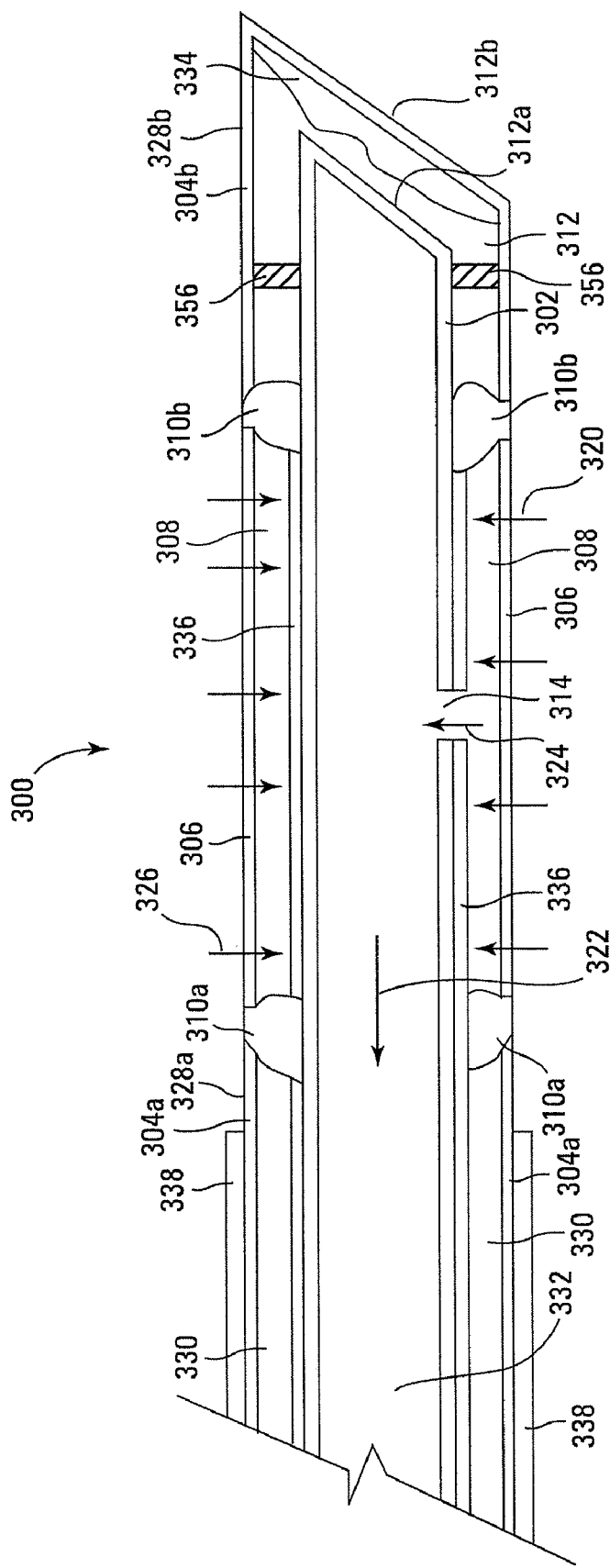
FIG. 2 is a cross sectional centerline view taken along the longitudinal axis of the injection/aspiration device shown in FIG. 1, having incorporated insulated metallic elements also functioning as electrodes, showing fluid from a patient passing through the semi-permeable membrane into the fluid collection chamber, resulting from negative pressure applied to the lumen.
Figure 7:
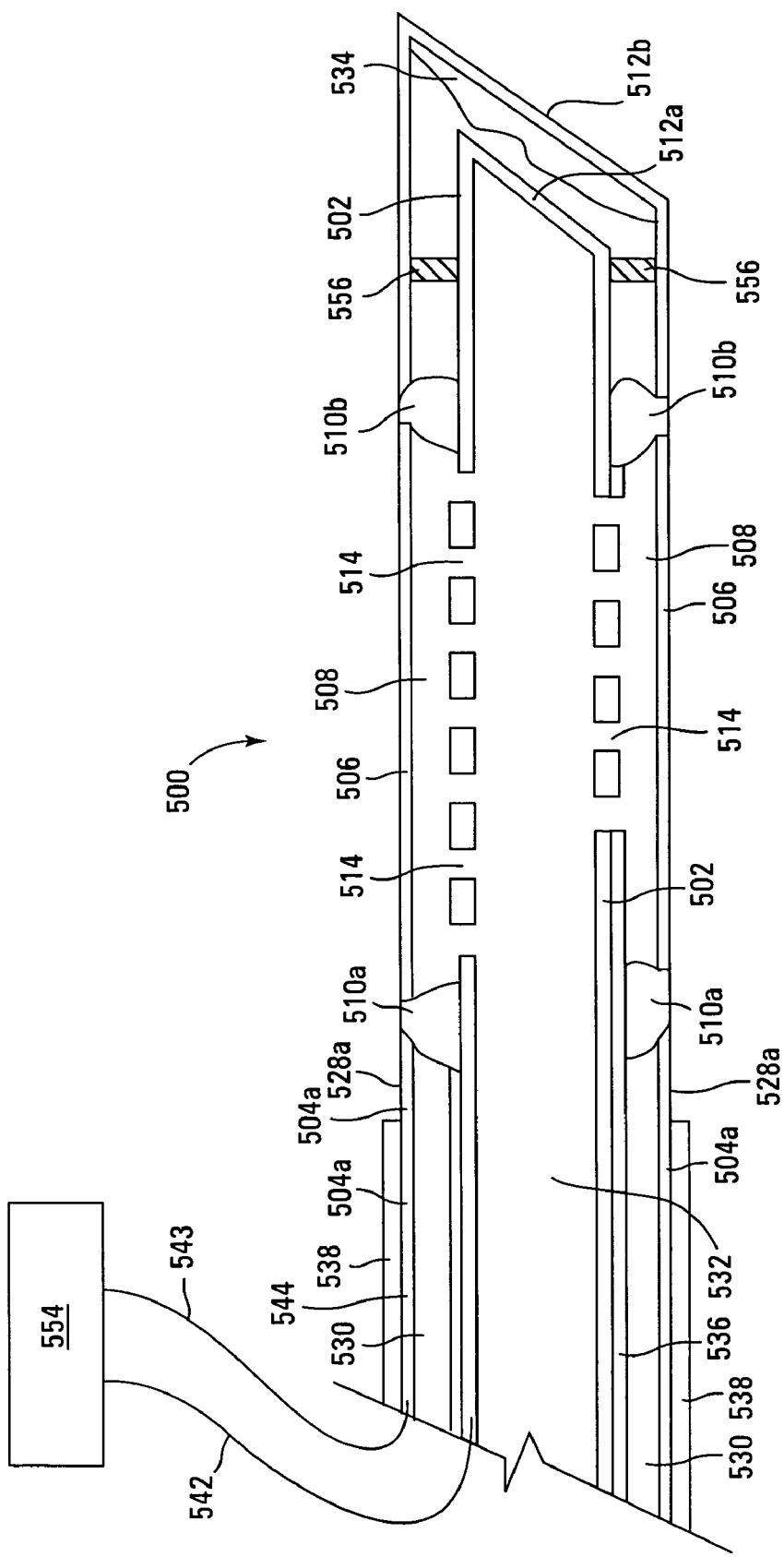
FIG. 7 is a cross sectional centerline view taken along the longitudinal axis of an embodiment of the injection/aspiration device having a plurality of openings in the first hollow member and is otherwise similar to the embodiment shown in FIGS. 1-6.

FIGS. 1 and 2 are cross sectional centerline views taken through the longitudinal axis (unnumbered) of an embodiment of the injection/aspiration device 300. A first hollow member 302 is formed from a conductive material such as structural materials with a high modulus including metals, conductive polymers (with and without fiber reinforcement) and defines a first lumen 332 which allows fluid communication through the first hollow member 302. A second hollow member is formed in a proximal section 304a and a distal section 304b which are substantially concentrically aligned with the first hollow member 302 which is disposed inside the proximal and distal sections 304a, 304b of the second hollow member. The proximal 304a and distal 304b sections of the second hollow member each define an outer surface 328a, 328b and are linearly disposed to and do not contact each other. The proximal 304a and distal 304b sections of the second hollow member function to stiffen the injection/aspiration device 300 which allows it to more effectively be introduced into a patient in some applications without the use of other devices such as a needle, cannula, catheter, trocar or introducer. A band of conductive material 356 at least partially surrounds the space (unnumbered) between the outer surface of first hollow member 302 and the distal section of the second hollow member 304b. The function of the conductive material 356 is to establish electrical communication between the first hollow member 302 and distal section of the second hollow member 304b which allows the outer surface of the distal section of the second hollow member 304b to function as an electrode. A semi-permeable membrane 306 covers at least part of the space between the proximal and distal sections 304a, 304b of the second hollow member to form a fluid collection chamber 308 between the first hollow member 302 and semi-permeable membrane 306 and is attached to the first hollow member 302 and proximal and distal sections of the second hollow member 304a, 304b by a bonding agent 310 such as structural adhesives including but not limited to epoxies, urethanes, acrylics, cyanoacrylates, polyimides and polysulfones. At least a single opening 314 is formed through the first hollow member 302 allowing fluid communication between the first lumen 332 and fluid collection chamber 308 as depicted by arrow 318 (arrow 324 in FIG. 2). While the exterior surface of the semi-permeable membrane 306 is shown in this embodiment as being co-planar with the exterior surfaces 328a, 328b of the proximal 304a and distal sections 304b of the second hollow member 304 the invention also contemplates having the semi-permeable membrane 306 placed on an interior surface (not shown) and is therefore within the scope of the invention. The distal end of the second hollow member 304b defines a distal end 312 which in this embodiment is sealed by plug 334. It is understood that while the injection/aspiration device 300 is shown as having a single opening 314 between the first hollow member 302 and the fluid collection chamber 308, this is for purposes of illustration only and therefore other configurations having a plurality of openings as shown in FIG. 7 is also within the scope of the invention.

Figure 6:
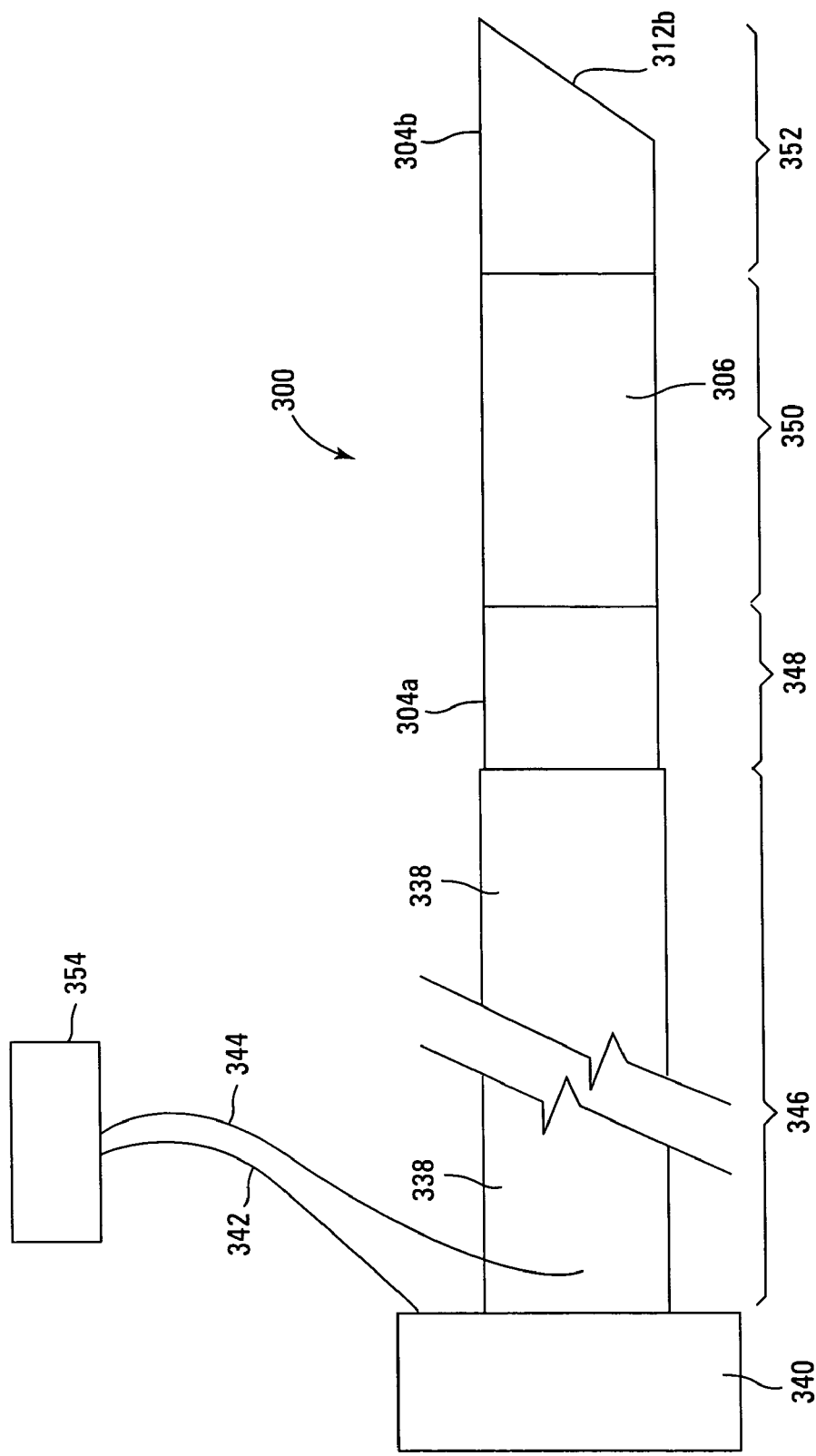
FIG. 6 is a broken side view of the injection/aspiration device shown in FIGS. 1-5.

A first insulator 336 surrounds the first hollow member 302 from its proximal end (not shown) to approximately the distal end (unnumbered) of the semi-permeable membrane 306. A second insulator 338 surrounds the proximal section of the second hollow member 304a from its proximal end (not shown) and terminates before the distal termination (unnumbered) of the proximal section of the second hollow member 304a. As shown in FIG. 6, a first electrical lead 342 is in electrical communication with the first hollow member 302 (attachment not shown) and a second electrical lead 344 is in electrical communication with the proximal section of the second hollow member 304a.

As discussed above, the first hollow member 302 and proximal and distal sections 304a, 304b of the second hollow members are typically formed from a conductive material such as tubular stainless steel. First hollow member 302 and proximal and distal sections 304a, 304b of the second hollow member are first cut to length followed by machining the ends for final uses that typically include a sharpened needle tip (unnumbered) used for penetrating tissue on the distal end 312b of the distal section 304b of the second hollow member and a fitting 340 on the proximal end. The opening 314 in the first hollow member 302 is created by conventional machine cutting tools (e.g., drill bits) or other types of hole-drilling processes such as laser machining. The first hollow member 302 is attached to the fitting 340 using a structural adhesive including but not limited to epoxies, urethanes, acrylics and polysulfones. Following this step, the first insulator 336 in one embodiment is slid over the first hollow member 302 and attached by an adhesive including but not limited to epoxy or cyanoacrylate. The first insulator is a polyfluoro carbon material including but not limited to PTFE and can be applied as a slid tube or sprayed on as a liquid and then cured. In another embodiment the first insulator 336 is a polyimide material or a polyester heat shrink material. Yet another suitable insulator material is a vacuum deposited parylene coating. The proximal section of the second hollow member 304a is next slid over the first insulator 336 and attached to the fitting 36 by a structural adhesive including but not limited to epoxies, urethanes, acrylics and polysulfones. A proximal layer of bonding agent 310a is applied between the proximal section of the second hollow member 304a and the first insulator 336 which not only serves to adhere the proximal section of the second hollow member 304a and the first insulator 336 together but also allows a degree of control over the internal configuration (e.g., concentricity) of those elements. It should be mentioned that the first insulator 336 and proximal section of the second hollow member 304a are not in contact with each other but in fact are separated by attachment on the fitting 340 at the proximal end and by the proximal layer of bonding agent 310a to form the second lumen 330. Next, the cut to length semi-permeable membrane 306 is slid over the first insulator 336 and adhered to the proximal layer of bonding agent 310a. Following this, a distal layer of bonding agent 310b is applied between the first insulator 336 and the semi-permeable membrane 306 which similarly serves to not only adhere the semi-permeable membrane 306 to the first insulator 336 but also allows a degree of control over the configuration thereof. The fluid collection chamber 308 is formed as the space between the first insulator 336 and semi-permeable membrane 306. The distal section of the second hollow member 304b is slid over the still exposed distal section (unnumbered) of the first hollow member 302 and affixed thereto by the distal layer of bonding agent 310b. If the sharpened distal end 312b of the second hollow member 304b has not been previously plugged 334 with a filling material such as structural adhesive, solder or brazing alloys as described above, it should be done as a last step. Finally, the first 342 electrical lead is attached to the first hollow member 302 and the second electrical lead 344 is attached to the proximal section of the second hollow member 304a, using methods well known to those having ordinary skill in the art including and not limited to soldering or fasteners. A band of conductive material 356 such as solder extends between the first hollow member 302 and the distal section of the second hollow member 304b. This establishes electrical communication and allows the distal section of the second hollow member 304b to function as an electrode, thus permitting the electric current used during an electroporation procedure to flow through tissue. It should be further mentioned that another embodiment of the device (not shown) could be made by eliminating the distal section of the second hollow member 304b wherein the exposed section of the first hollow member 302 would act as an electrode.

The injection/aspiration device 300 shown in FIG. 1 is depicted by arrow 316 as having positive pressure applied to the first lumen 332. This results in fluid (not shown) moving distally through the first lumen 332 and ultimately through the opening 314 (as depicted by arrow 318), into the fluid collection chamber 308 and finally outward through the porous semi-permeable membrane 306 at a controlled flow and distribution as depicted by arrow 320 to the intended treatment site of the patient following introduction of the device 300.

The injection/aspiration device 300 shown in FIG. 2 is depicted by arrow 322 as having negative pressure applied to the first lumen 332. This results in fluid (not shown) moving through the semi-permeable membrane 306 as depicted by arrow 326, into the fluid collection chamber 308, through the opening 314 (as depicted by arrow 324), and finally into the lumen 332 where the fluid (not shown) is withdrawn.

Figure 3:
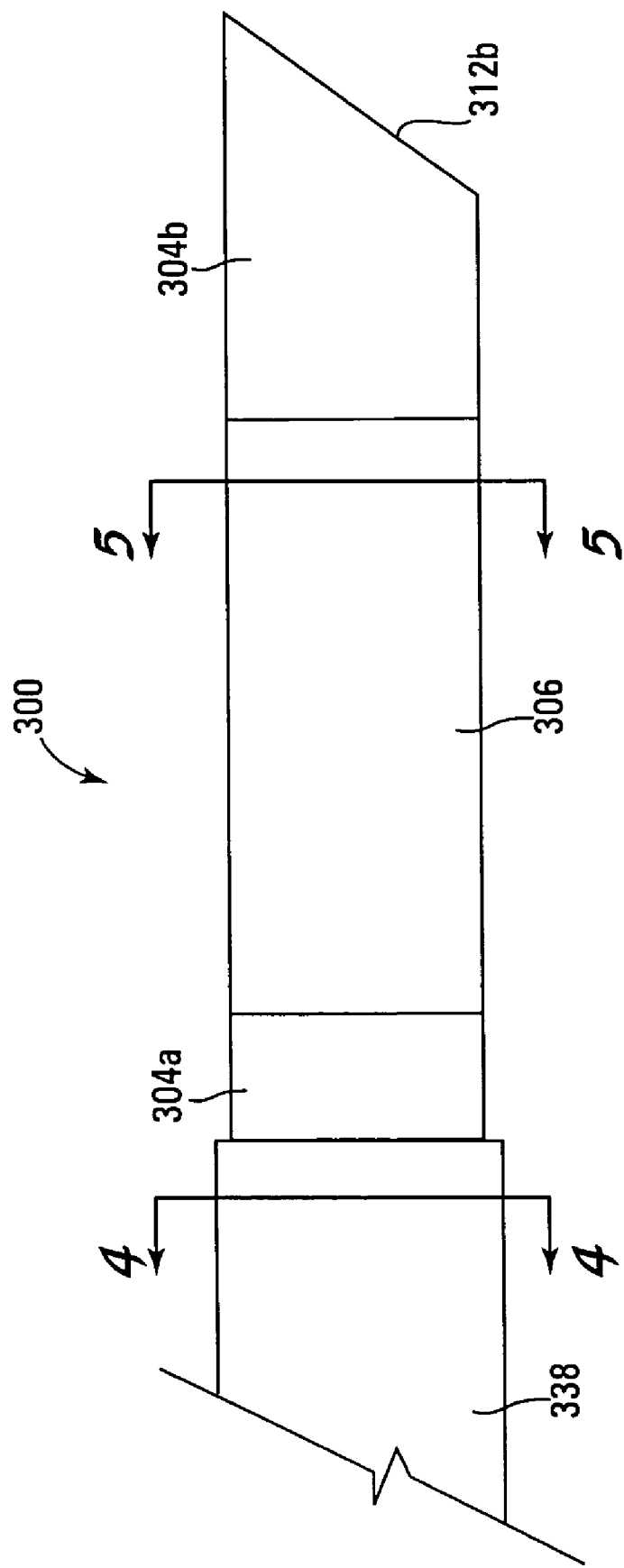
FIG. 3 is an external side view of the injection/aspiration device shown in FIGS. 1-2.

FIG. 3 is an external side view of the injection/aspiration device 300 prior to use. It is seen that the proximal 304a and distal 304b sections of the second hollow member are linearly separated by the semi-permeable membrane 306. The semi-permeable membrane 306 and proximal 304a and distal 304b sections of the second hollow member are attached to the first hollow member 302 (not shown in this figure) by means of a bonding agent 310. It is understood that the proximal end of the device (not shown) is fitted with a fitting 340 such as a Luer, barbed or tapered tube fitting, allowing it to be connected with a fluid supply (not shown) or pressure generating device such as a syringe 40. It is further understood that the device could also be connected with a vacuum or aspirating device such as a mechanical pump (not shown), or hand operated syringe 40 when the device 300 is used for aspirating fluids.

Figure 4:
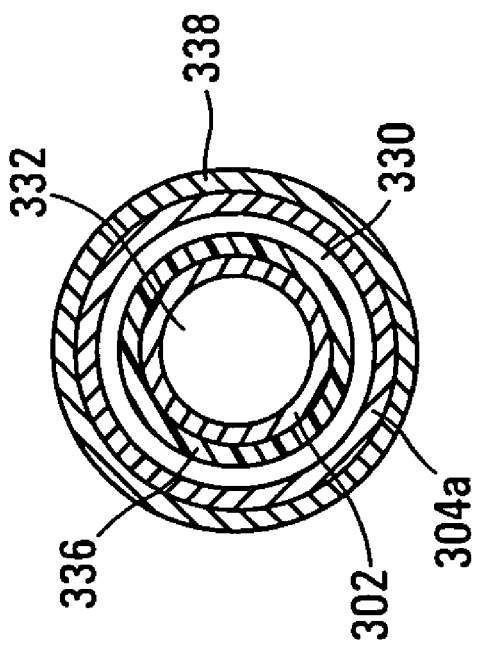
FIG. 4 is a cross sectional view of the injection/aspiration device shown in FIGS. 1-3 taken through line 4-4 of FIG. 3.

FIG. 4 is a cross sectional view of the injection/aspiration device shown in FIGS. 1-3 taken through line 4-4 as shown in FIG. 3. At the point where the cross section is taken it is seen that the outermost layer is the second insulator 338 which serves to insulate the proximal section 304a of the second hollow member, which is the next layer. The second lumen 330 is formed between the proximal section 304a of the second hollow member and the first insulator 336 and serves no purpose. The first insulator 336 surrounds the first hollow member 302 which is the innermost component at the point the cross section is taken and defines the first lumen 332. The first hollow member 302 and proximal section 304a of the second hollow member in this embodiment are made of an electrically conducting material such as metals or electrically conductive polymers. The first 336 and second 338 insulators function to keep the electrical contacts (the first hollow member 302 and proximal section 304a of the second hollow member) from making contact with each other during the procedure, allowing an electric signal to flow between the electrical contacts (the first hollow member 302 and proximal section 304a of the second hollow member) during the procedure, thus permitting a degree of accuracy as to where the electrical pulse is delivered. As discussed in greater detail below, certain procedures such as electroporation require a mild electric potential or current to flow through an area of the patient's anatomy.

Figure 5:
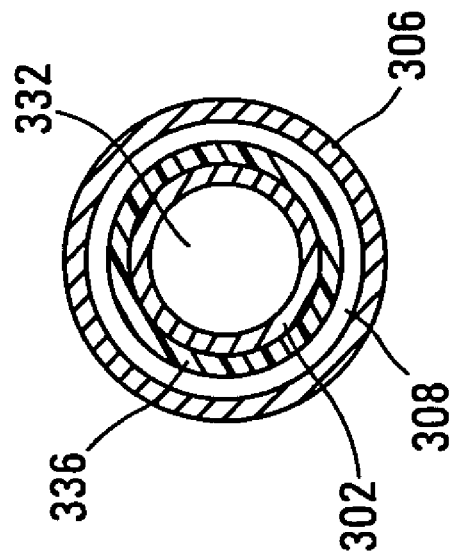
FIG. 5 is a cross sectional view of the injection/aspiration device shown in FIGS. 1-3 taken through line 5-5 of FIG. 3.

FIG. 5 is a cross sectional view of the injection/aspiration device shown in FIG. 5 taken through line 5-5 as shown in FIG. 3. At the point where the cross section is taken it is seen that here the outermost layer is the semi-permeable membrane 306. The fluid collection chamber 308 is formed between the semi-permeable membrane 306 and the first insulator 336. The first insulator 336 surrounds the first hollow member 302, which defines the first lumen 332.

Figure 6A:
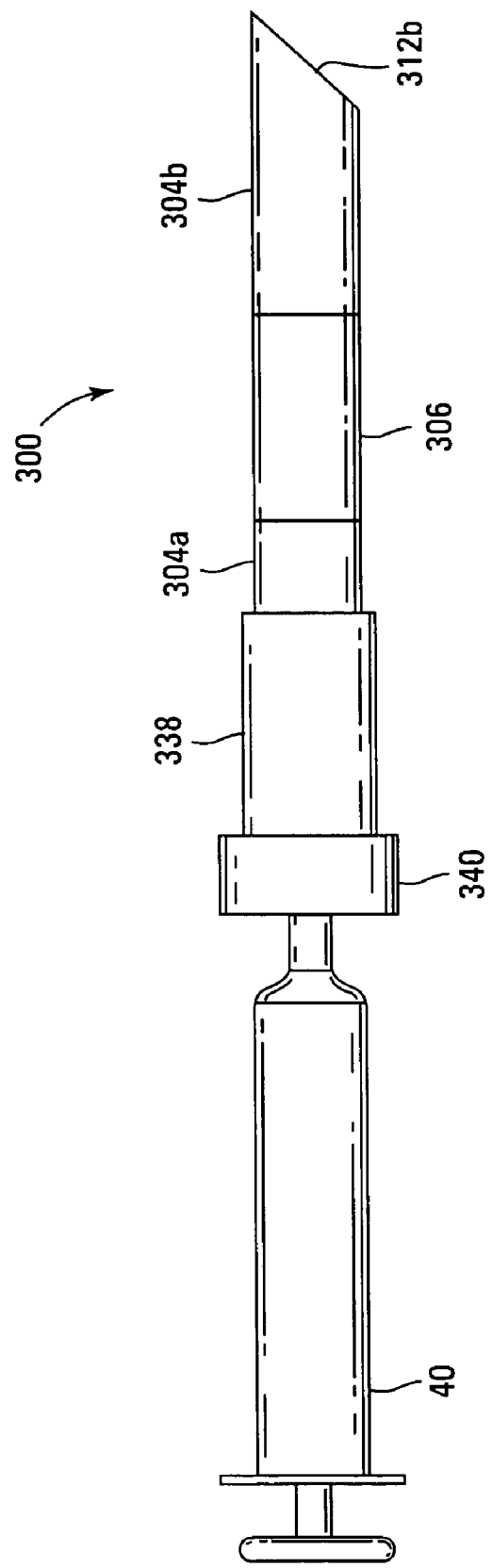
FIG. 6A is an external side view of the injection/aspiration device shown in FIGS. 1-6, coupled to a syringe.

FIG. 6 shows a side, external view of the conducting injection/aspiration device 300. It is seen that the injection/aspiration device 300 comprises a proximal section 346 which extends distally from approximately the fitting 340 to approximately a point proximal (unnumbered) of an external electrical contact section 348. The external electrical contact section 348 is the uninsulated distal end (unnumbered) of the proximal section of the second hollow member 304a and functions as an electrode during electroporesis procedures as discussed herein. A semi-permeable membrane section 350 extends approximately distally from a distal end (unnumbered) of the external electrical contact section 348 approximately to the proximal end (unnumbered) of a distal section 352 and comprises the exposed portion of the semi-permeable membrane 306. The distal section 352 comprises the distal section of the second hollow member 304b and extends distally from approximately the distal termination of the semi-permeable membrane section 350 to the distal end 312b of the second hollow member 304b. First 342 and second 344 electrical leads are in electrical communication with the first hollow member 302 and proximal section of the second hollow member 304a. When an electroporesis treatment is performed the first 342 and second 344 electric leads are attached to a power source 354 such as a battery or DC power supply and energized, as discussed in greater detail as described herein, following introduction. FIG. 6A shows a syringe 40 coupled to the fitting 340.

Figure 7A:
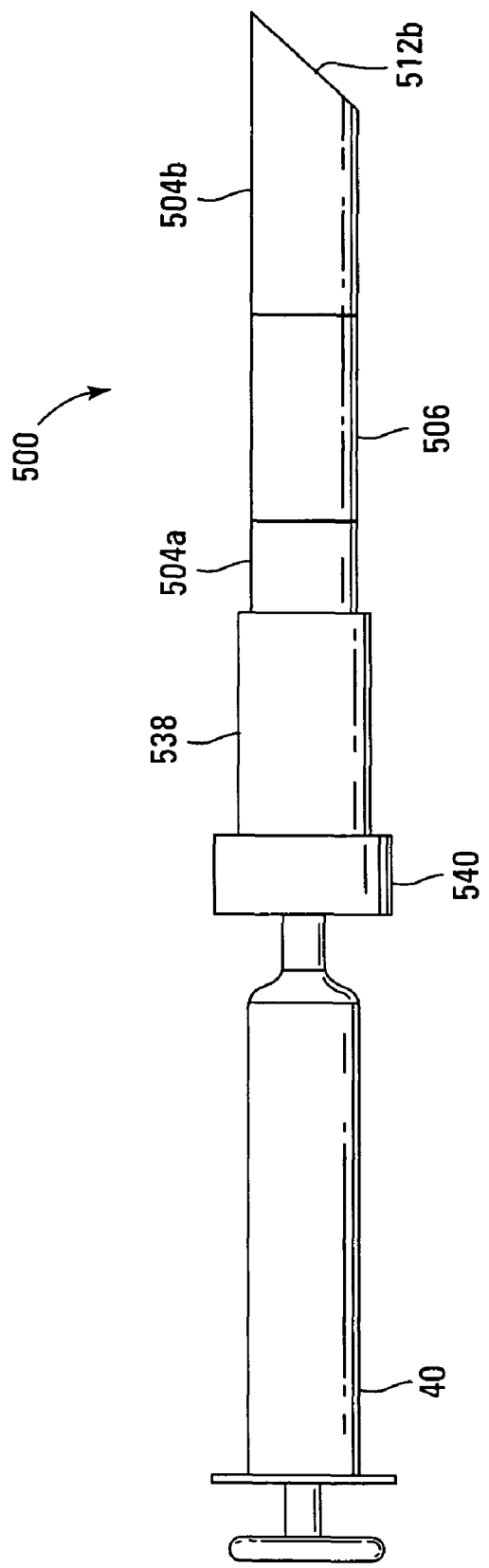
FIG. 7A is an external side view of the injection/aspiration device shown in FIG. 7, coupled to a syringe.

FIG. 7 is a cross sectional centerline view taken through the longitudinal axis of the hollow member of an embodiment of the injection/aspiration device 500 having a plurality of openings 514 in the first hollow member 502. Other than having a plurality of openings 514 the injection/aspiration device 300 is similar to the injection/aspiration device 300 shown in FIGS. 1-6. FIG. 7A shows a syringe 40 coupled to the fitting 540.

Figure 8:
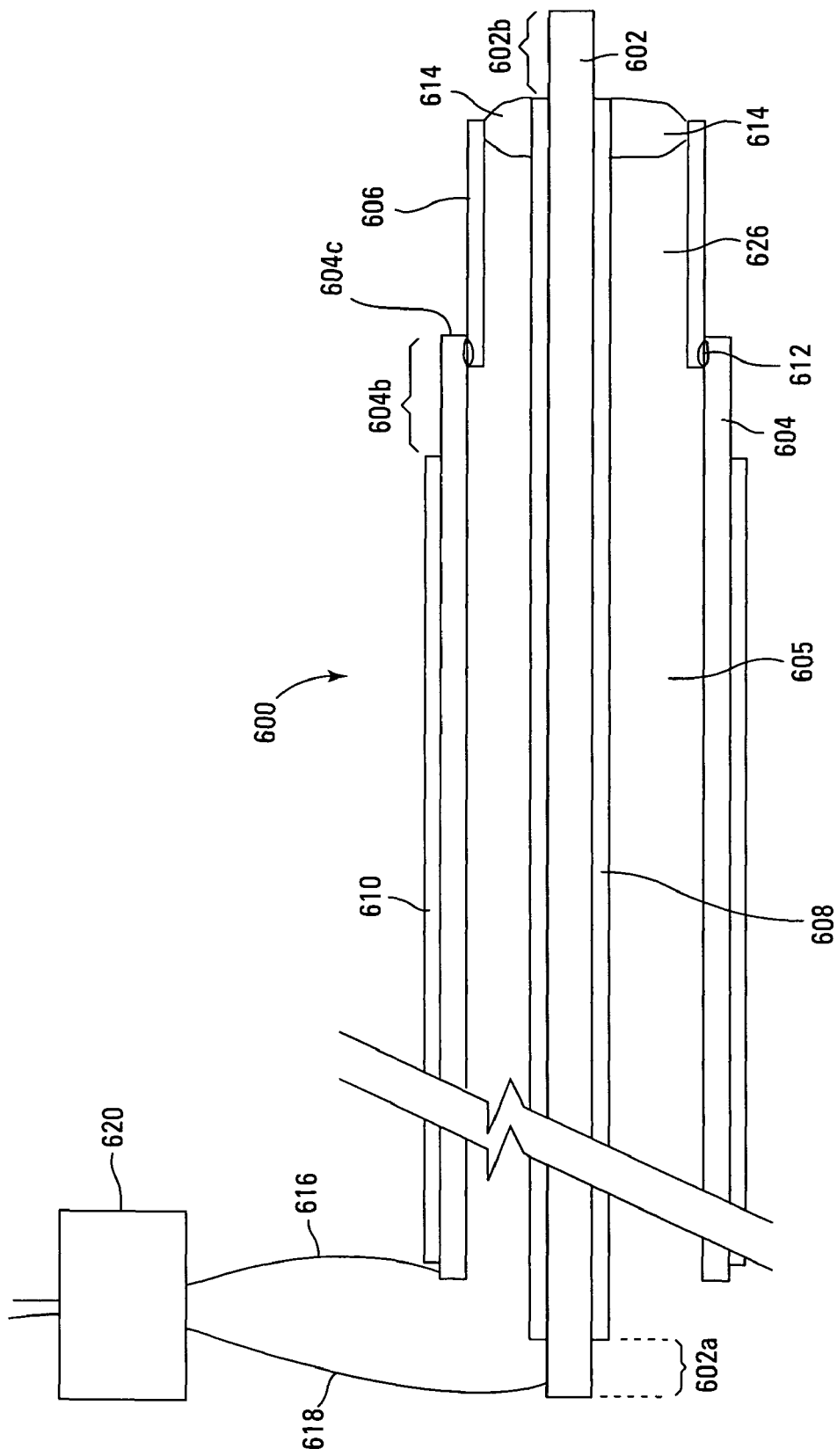
FIG. 8 is a cross sectional centerline view taken through the longitudinal axis of an embodiment of the injection/aspiration device.

FIG. 8 is a cross sectional centerline view taken through the longitudinal axis of an embodiment of the injection/aspiration device 600. The embodiment shown in FIG. 8 has a solid member 602 extending along the longitudinal axis of the device. Suitable materials for the solid member 602 include, but are not limited to, stainless steel, platinum alloy or any electrically conductive material. The solid member 602 is covered by a first insulator 608 which extends along most of its length leaving an exposed proximal end 602a and exposed distal end 602b of the solid member. The first insulator 608 functions to maintain the solid member 602 in a non-conductive state from the rest of the device 600. A hollow member 604 defines a lumen 605 through which is fitted the solid member 602 and its covering first insulator 608. Suitable materials for the hollow member 604 include, but are not limited to, stainless steel and other tubing having conductive properties. The hollow member 604 is covered by a second insulator 610 which ends proximally of the termination of the hollow member 604c leaving an exposed distal end 604b. The solid member 602 and hollow member 604 are made of an electrically conductive material such as metallic materials or conductive polymers, thus the exposed distal end 602b of the solid member 602 and exposed distal end 604b of the hollow member 604 are able to function as electrodes. A first electrical lead 616 is connected to the hollow member 604 and a second electrical lead 618 is connected to the solid member 602. The first 616 and second 618 electrical leads are attached to a power source 620 during a procedure requiring an electrical signal, which is discussed in greater detail below. The first 608 and second 610 insulators function to keep the electrical contacts (the distal end 602b solid member 602 and distal end 604b of the hollow member 604) from making contact with each other during the procedure, allowing an electric signal to flow between the electrical contacts (the distal end 602b solid member 602 and distal end 604b of the hollow member 604) through tissue during the procedure. As discussed in greater detail below, certain procedures such as electroporation require a mild electric potential or current to flow through an area of the patient's anatomy. A semi-porous membrane 606 is attached to and extends from the distal termination 604c of the hollow member 604. The section of the semi-permeable membrane 606 which extends beyond the distal termination 604c of the hollow member 604 is attached to the hollow member 604 by a proximal layer of bonding agent 612 which serves to both secure in place and seal the semi-permeable membrane 606 to the hollow member 604. A distal layer of bonding agent 614 similarly serves to secure in place and seal the first insulator 608 to the semi-permeable membrane 606. The bonding agent 612, 614 includes but is not limited to structural adhesives such as epoxies, urethanes, acrylics, polyimides and polysulfones. The section of the semi-permeable membrane which extends beyond the distal termination of the hollow member 604 is in fluid communication with the lumen 605 and forms a fluid collection chamber 626 through which fluid may pass in a controlled and gentle manner.

The solid member 602 is first cut to length by conventional methods. The first insulator 608 is slid or sprayed over the cut solid member 602 and then trimmed for length. The first insulator 608 is a polyfluoro carbon material including but not limited to PTFE and can be applied as a tube, shrink-wrap material, sprayed on as a liquid or applied by vacuum deposition and then cured. The first insulator can also be made from a material such as polyimide. Solid member 602 and first insulator 608 together form an inner subassembly (not shown). An outer subassembly (not shown) is next created by cutting to length the hollow member 604 using conventional methods followed by sliding or spraying the second insulator 610 over it, making sure a section at the distal end 604b of the hollow member 604 is left uninsulated to be able to later function as an electrode. Following creation of the outer subassembly (not shown) the cut to length semi-permeable membrane 606 is placed on a removable mandrel (not shown) and bonded to the distal end of the hollow member 604. The mandrel (not shown) provides support and also prevents buildup of the bonding agent (not shown) to the surface of the semi-permeable membrane 606, which could later reduce performance. Upon curing of the bonding agent (not shown) the mandrel is removed. The outer subassembly (not shown) is then bonded to the fitting 622 at the distal end (unnumbered) of the fitting. Finally, the inner subassembly (not shown) is slid into the outer subassembly (not shown) and bonded at the proximal end (unnumbered) of the fitting 622 and bonded 614 at the distal end of the semi-permeable membrane 606. The finished device 600 provides electrodes as the uninsulated distal end 604b of the hollow member 604 and the uninsulated distal end 602b of the solid member 602.

Figure 9:
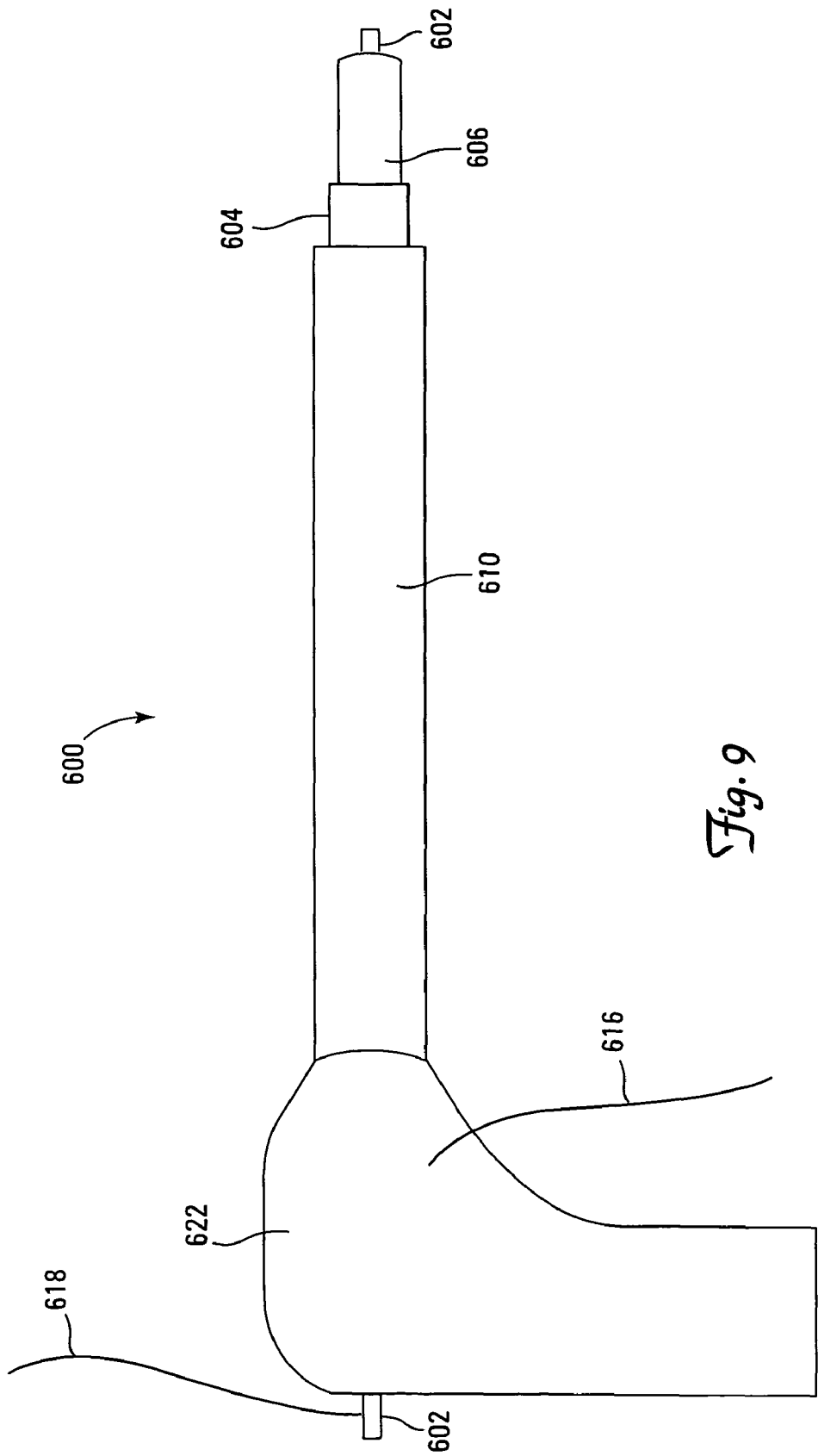
FIG. 9 is a side external view of the embodiment of the injection/aspiration device shown in FIG. 8.
Figure 9A:
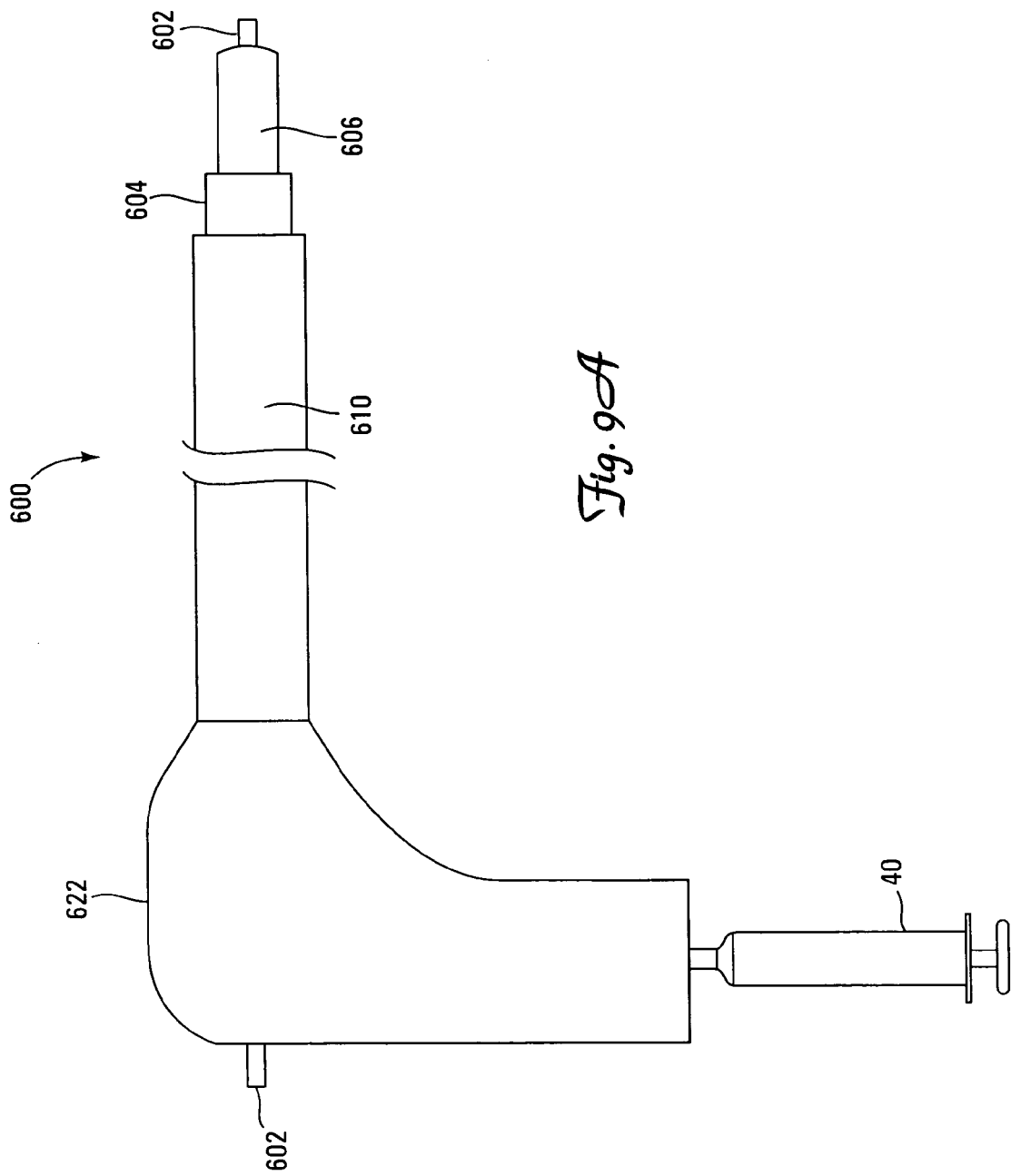
FIG. 9A is an external side view of the injection/aspiration device shown in FIG. 9, coupled to a syringe.

FIG. 9 is a side external view of the embodiment of the injection/aspiration device 600 shown in FIG. 8. It is seen that the proximal section of the device 600 is provided with a non-conductive fitting 622 which serves to separate and solidly mount the various components. A fluid conduit 624 extends from the fitting 622 into the lumen 605 and allows for fluid communication between an external source (not shown), the lumen 605 of the hollow member 604 and eventually the fluid collection chamber 626. FIG. 9A shows a syringe 40 coupled to the fitting 622.

Figure 10:
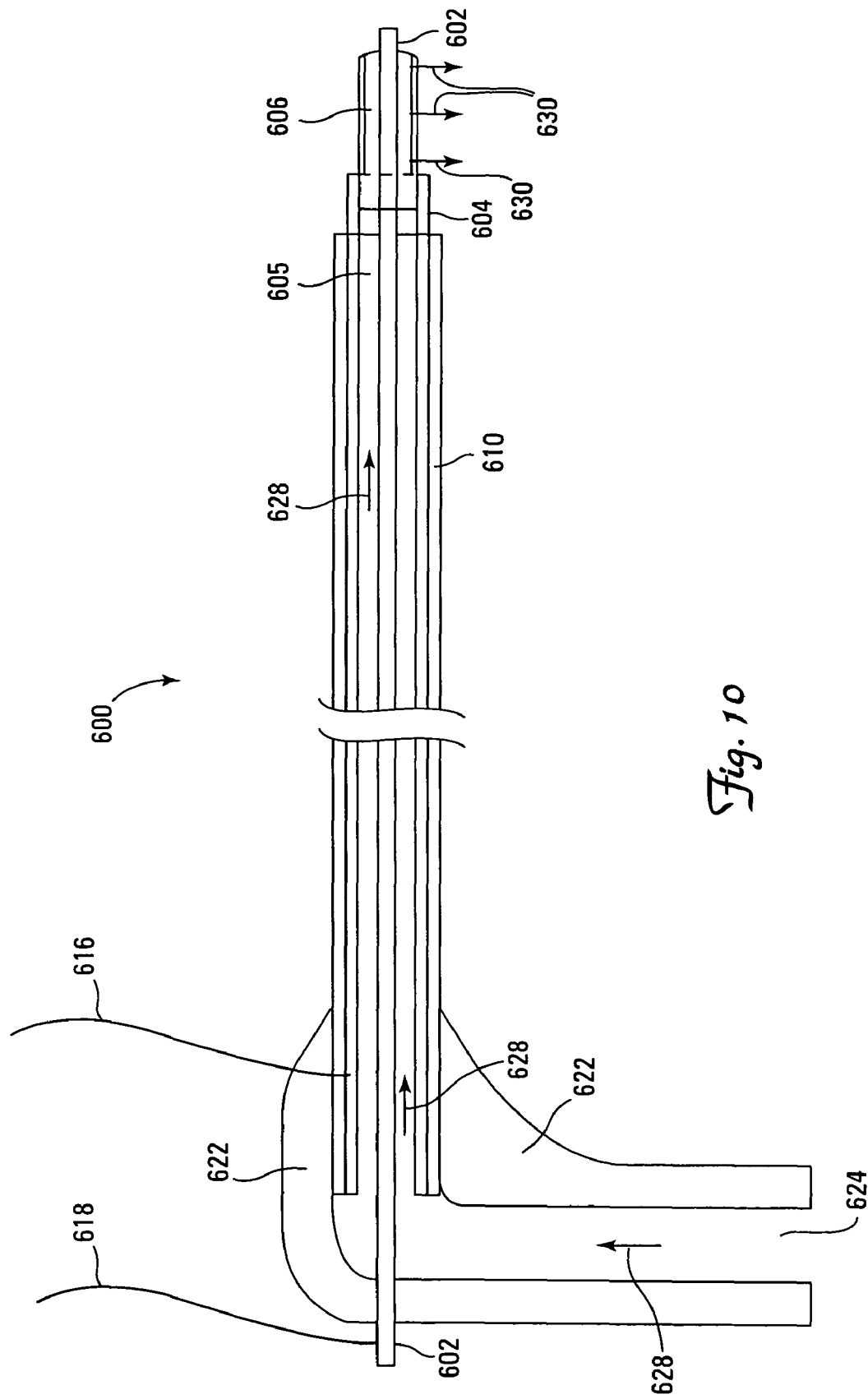
FIG. 10 is a cross sectional centerline view taken through the longitudinal axis of the embodiment of the injection/aspiration device shown in FIGS. 8-9, showing fluid passing through the semi-permeable membrane resulting from positive pressure applied to the lumen.

FIG. 10 is a cross sectional centerline view taken through the longitudinal axis of the embodiment of the injection/aspiration device shown in FIGS. 8-9, showing fluid passing through the semi-permeable membrane 606 resulting from positive pressure applied to the lumen 605. Positive pressure as depicted by arrow 628 is applied through the fluid channel 624 which extends through the fitting 622 and is in fluid communication with the lumen 605. The lumen 605 at its distal end (unnumbered) is in fluid communication with the fluid collection chamber 626 which is formed by the attachment of the hollow semi-permeable membrane 606 to the distal end of the hollow member 604. Positive fluid pressure as depicted by arrow 628 is applied through the fluid channel 624 to the lumen 605 and eventually to the fluid collection chamber 626. Fluid is propelled by the positive pressure causing it to pass through the semi-permeable membrane 606, as depicted by arrow 630.

FIG. 11 is a cross sectional centerline view taken through the longitudinal axis of an embodiment of the injection/aspiration device shown in FIGS. 8-10, showing fluid from a patient passing through the semi-permeable membrane 606 into the fluid collection chamber 626, resulting from negative pressure applied to the lumen 605. Negative fluid pressure as depicted by arrow 632 is applied through the fluid channel 624 which extends through the fitting 622 and is in fluid communication with the lumen 605. The lumen 605 at its distal end (unnumbered) is in fluid communication with the fluid collection chamber 626 which is formed by the attachment of the hollow semi-permeable membrane 606 to the distal end of the hollow member 604. As depicted by arrow 634, fluid is drawn through the semi-permeable membrane 606 into the fluid collection chamber 626 and eventually into the lumen 605. From the lumen 605 the fluid is drawn into the fluid channel 624 out of the device 600 and disposed of.

When the injection/aspiration device 300, 500, 600 is used for electroporation, an electric signal having a voltage differential ranging between about 1 to 2000 mV/cm$^2$, with a preferable range of 5 to 1000 mV/cm$^2$, is sent through the second electrical lead 344 544, 618 from a power source 354, 554, 620. A recommended pattern of applying the electric signal is one such as exponential logarithmic wave forms or square wave forms, but is not limited to those. In another embodiment the electrical signal may be pulsed, i.e., periodically turned on and off or varied in intensity. The electric signal for electroporation is preferably applied one or more times. Following patient introduction, the electric signal flows through tissue from the second hollow member 304a, 504a or hollow member 604 to the first hollow member 302, 502 or solid member 602. The electric signal causes an increase in cellular permeability due to the process of forming very small openings (pores) in the plasma semi-permeable membrane, which increases the body's ability to absorb the therapeutic agent which flows from the first lumen 332, 532 through the opening 314, 514 into the fluid collection chamber 308, 508 and eventually out through the semi permeable membrane 306, 506 to the treatment site. In the case of the injection/aspiration device 600 shown in FIGS. 8-11, the therapeutic agent flows through the lumen 605 to the fluid collection chamber 626, where, under positive fluid pressure, it is evenly distributed to the desired treatment site.

The injection/aspiration device 300, 500, 600 which is provided with insulated electrically conductive elements 302, 304b, 502, 504b, 602, 604 which are able to function as electrodes. It should also be mentioned that, in addition to electroporation procedures, the electrodes can also be used in conjunction with various sensing devices, for example to determine whether the device 300, 500, 600 is in contact with muscle, fat or nerve tissue. A mild electric signal is sent to the electrodes with a varying response received depending on what kind of tissue is contacted.

In one embodiment, the semi-permeable membrane 306, 506, 606 can be made from a hollow fiber. Suitable materials for use as hollow fibers of the present invention provide an optimal combination of such properties as mass transfer properties, biocompatibility, surface-to-volume ratio, processability, hydrophobicity/hydrophilicity, strength, transport rate, and porosity. Examples of suitable hollow fibers are described in, for instance, I. Cabasso, "Hollow-Fiber Semipermeable membranes", pp 598-599 in *Kirk Othmer Concise Encyclopedia of Chemical Technology*.

The dimensions of a hollow fiber will depend largely on the intended use of the apparatus. In a number of preferred embodiments, a hollow fiber will be provided in the form of a capillary having an outer diameter of less than about one centimeter, and preferably less than about three millimeters, and whose outer, tissue contacting, wall functions as a semipermeable membrane. In most cases, a hollow fiber will be used as a cylindrical semi-permeable membrane in a manner that permits selective exchange of materials across its walls.

In another embodiment, the semi-permeable membrane 306, 506, 606 can be a modified microcatheter. Modified microcatheters can be prepared in any suitable manner, e.g., by microperforating an otherwise intact capillary or by spinning hollow fiber semi-permeable membranes from natural or synthetic polymers. Such fibers can be formed having any desired characteristics, e.g., isotropic (dense or porous) and anisotropic (asymmetric). Examples of suitable materials for use as microcatheters of this invention include, but are not limited to, microinfusion tubing such as polyethylene tubing available from Clay Adams under the designations PE-10 (0.28 mm/0.61 mm, inner and outer diameters), PE-20 (0.38 mm/1.09 mm), PE-50 (0.58 mm/0.965 mm) and PE-90 (0.86 mm/1.27 mm). Such tubing can be microperforated by any suitable means, such as lasers and the like. Other examples of suitable materials include membrane fibers such as those identified in the following table:

| Types | Manufacturer | Catalog No. | Interior Diameter (um) | Wall Thickness (um) | Flow Rate (mL/min)/ Surface Area (sq. meter) | Porosity |
|---|---|---|---|---|---|---|
| Cuprophan | Baxter Haemodialysis Products | unknown | 200 | 8 | unknown | |

-continued

| Types | Manufacturer | Catalog No. | Interior Diameter (um) | Wall Thickness (um) | Flow Rate (mL/min)/ Surface Area (sq. meter) | Porosity |
|---|---|---|---|---|---|---|
| Hemophan FoCus 160-H | Baxter Haemodialysis Products | unknown | 200 | 8 | unknown | |
| Spectra/Por Regenerated Cellulose Polyethylene Polypropylene Polysulfone | Spectrum 23022 La Cadena Drive, Suite #100 Laguna Hills, Ca. 92653 | #132-200 through 132-313 membrane types vary according to m.w., volume, pH, and chemical compatibility | 200 380 500 | 10-20 25 75 | 25-15 | 0.5 um 50 nm |
| Cellulose Triacetate CT-190 | Baxter Haemodialysis Products | CT-190 series #5M1546 CT-110-190 also available | 200 | unknown | unknown | |
| Cellulose Acetate CA-170 | Baxter Haemodialysis Products | CA-170 series #5M-1735 CA-150 - CA-170 series also available | unknown | unknown | unknown | |
| Polysulfone Hemoflow F-60A High Flux | Fresenius | F60 series #0500136A F3-6, 8, 40-80 series also available | 200 | 40 | 40/1.3 | |
| Polysulfone Polyphen Capillary Membrane | Minntech | | 280 | 40 | | 0.45 um 0.10 um |
| Polyacrylo-nitrile (PAN) | Gambro-Health | | unknown | unknown | unknown | |
| Polyimide | UBE | unknown | unknown | unknown | unknown | unknown |
| Polysulfone | GE Healthcare | unknown | 0.5 mm (.45 um) 0.75 mm (.65 um) | unknown | unknown | 500,000 mwco |
| PVDF Polysulfone PAN | Koch | Unknown Unknown unknown | 0.5 mm & larger .043 inch | unknown | unknown | Up to 0.2 um Up to 500,000 mwco |
| PES-phylic -phobic PVDF | Membrana | Unknown Unknown unknown | 300 350 unknown | 100 85 unknown | unknown | 0.5 um 0.5 um unknown |
| PVDF PP | Memcor/US filter | Unknown unknown | 500 unknown | 150 unknown | unknown | 0.04 to 0.1 um 0.1 um |

It should also be mentioned that the device 300, 500, 600 can also be used in pairs where a first device 300, 500, 600 is introduced into a patient followed by introduction of a second device 300, 500, 600 into the patient and placed in close proximity to but not contacting the first device 300, 500, 600. A negative terminal is attached to one device 300, 500, 600 and a positive terminal is attached to the other device 300, 500, 600 followed by an electroporation procedure. It is further contemplated that such a procedure would require a device having only one insulated electrode (not shown).

Use

Using the injection/aspiration device 300, 500, 600 involves first preparing the patient for the procedure. Next, the device 300, 500, 600 is removed from its sterile packaging. In some procedures, depending on tissue hardness and/or density, the device 300, 500, 600 is inserted through the patient's skin at a point convenient and proximate to the internal site of treatment. In most cases, depending on tissue density, the inherently rigid nature of the device 300, 500, 600 allows direct insertion through the patient's skin and other underlying soft tissue without the use of an additional introduction device such as a cannula, trocar, catheter, guide catheter, guide wire or other introducer. Obviating additional introducing devices necessitates shorter treatment times, decreased expense and a lesser probability of infection. In addition, introduction without introducing devices decreases the size of tissue access opening to the treatment site, thereby decreasing the morbidity, invasiveness and pain associated with the procedure. Other procedures, however, may require the use of an introducing device such as a cannula, trocar, catheter, guide catheter, guide wire or other introducer.

When the desired treatment site is accessed for a procedure requiring positive fluid pressure, the device 300, 500, 600 is connected to a fluid supply and/or pressure generating device such as a syringe 40 which has been preloaded with a drug or therapeutic fluid required by the procedure. Placement of the device 300, 500, 600 is determined to be correct by such methods as anatomical landmarks, ultrasound, CT guided introduction, MRI guided introduction, or an electrical signal. Positive pressure is applied to the first lumen 332, 532 or lumen 605 initially filling the empty lumen with the drug or therapeutic fluid. When the first lumen 332, 532 or lumen 605 is filled, the drug or therapeutic fluid is forced through the opening or openings 314, 514, and into the fluid collection chamber 308, 508 or directly into the fluid collection chamber 626. The fluid collection chamber 308, 508, 626 fills with the drug or therapeutic fluid which initially impedes flow and therefore buffers and equalizes the pressure and distribution of the weep rate of fluid from the device 300, 500, 600. The drug or therapeutic fluid is eventually gently forced out through the porous semi-permeable membrane 306, 506, 606 outside the device 300, 500, 600 where it is taken up over a relatively large surface area of the surrounding tissues as required for treatment. An electric signal having a voltage differential ranging between about 1 to 2000 mV/cm$^2$, with a preferable range of 5 to 1000 mV/cm$^2$, is sent through the second electrical lead 344 544, 618 from a power source 354, 620. The electric signal can be impressed as an exponential logarithmic wave form or square wave form, but is not limited to those. In another embodiment the electrical signal may be pulsed, i.e., periodically turned on and off or varied in intensity. The electric signal for electroporation is preferably applied one or more times. The electric signal flows from the second hollow member 304a, 504a or hollow member 604 to the first hollow member 302, 502 or solid member 602. The electric signal causes an increase in cellular permeability due to the process of forming very small openings (pores) in the plasma semi-permeable membrane, which increases the body's ability to absorb the therapeutic agent which flows from the first lumen 332, 532 through the opening 314, 514 into the fluid collection chamber 308, 508 and eventually out through the semi permeable membrane 306, 506 to the treatment site. In the case of the injection/aspiration device 600 shown in FIGS. 8-11, the therapeutic agent flows through the lumen 605 to the fluid collection chamber 626, where, under positive fluid pressure, it is distributed to the desired treatment site. Following completion of the procedure the device 300, 400, 600 is removed from the patient, disconnected from the fluid supply and/or pressure generating device and disposed of.

When the desired treatment site is accessed for a procedure requiring negative fluid pressure, such as aspiration of excess fluid, the device 300, 500, 600 is connected to a vacuum or aspirating device such as a mechanical pump or hand operated syringe 40. Placement of the device 300, 500, 600 is determined to be correct by such methods as anatomical landmarks, ultrasound, CT guided introduction, MRI guided introduction, or an electrical signal. Negative pressure is applied to the first lumen 332, 532 or lumen 605 which extends to the fluid collection chamber 308, 508, 626. A negative pressure potential is created which allows fluid surrounding the outer surface and region of the semi-permeable membrane 306, 506, 606 to be drawn through the semi-permeable membrane 306, 506, 606 through the opening or openings 314, 514 into the first lumen 332, 532. In the case of the device 600 the fluid flows directly through the semi-permeable membrane 606 into the lumen 605. Once in the first lumen 332, 532 or lumen 605 the fluid is proximally transported outside the device 300, 500, 600 where it is disposed of or stored for further analysis. Following completion of the procedure the device 300, 500, 600 is removed from the patient, disconnected from the fluid supply and/or pressure generating device and disposed of.

When the desired treatment site is accessed for an electroporation procedure requiring positive fluid pressure, the device 300, 500, 600 is connected to a fluid supply and/or pressure generating device such as a syringe 40 which has been preloaded with a drug or therapeutic fluid required by the procedure. Placement of the device 300, 500, 600 is determined to be correct by such methods as anatomical landmarks, ultrasound, CT guided introduction, MRI guided introduction, or an electrical signal. Infusion of the drug or therapeutic fluid occurs by the application of positive pressure to the fluid supply and/or pressure generating device. Performing an electroporation procedure can be done by either (1) first infusing the treatment site with the drug or therapeutic fluid followed by impressing an electric signal through the device 300, 500, 600, or (2) simultaneously infusing the treatment site with the drug or therapeutic fluid and impressing an electric signal through the device 300, 500, 600. Positive pressure is applied to the first lumen 332, 532 or lumen 605 initially filling the empty first lumen 332, 532 or lumen 605 with the drug or therapeutic fluid. When the first lumen 332, 532 lumen 605 is filled, the drug or therapeutic fluid is forced through the opening or openings 314, 514 into the fluid collection chamber 308, 508. In the case of the device 600 the drug or therapeutic fluid flows directly through the lumen 605 to the fluid collection chamber 626. The fluid collection chamber 308, 508, 626 fills with the drug or therapeutic fluid which initially impedes flow and therefore buffers and equalizes the pressure and distribution of the weep rate of fluid from the device 300, 500, 600. The drug or therapeutic fluid is eventually gently forced out through the porous semi-permeable membrane 306, 506, 606 outside the device 300, 500, 600 where it is evenly distributed to and taken up by a relatively large surface area of the surrounding tissues as required for treatment. An electric signal having a voltage differential ranging between about less than 1 to 2000 mV/cm$^2$, with a preferable range of less than 5 to 1000 mV/cm$^2$, is sent through the second electrical lead 344, 544, 618 from a power source 354, 554, 654. A recommended pattern of impressing the electric signal is one such as exponential logarithmic wave forms or square wave forms, but is not limited to those. The electric signal for electroporation is preferably applied one or more times. The electric signal flows from the proximal section of the second hollow member 304a, 504a or distal end of the hollow member 604b to the first hollow member 302, 502 or distal end of the solid member 602b. It should be mentioned that the polarity of the electrodes can be reversed if the procedure requires it. The electric signal causes an increase in cellular permeability due to the process of forming very small openings (pores) in the plasma semi-permeable membrane, which increases the body's ability to absorb the therapeutic agent which flows from the first lumen 332, 532 through the opening 314, 514 into the fluid collection chamber 308, 508 and eventually out through the semi permeable semi-permeable membrane 306 to the treatment site. In the case of the device 600 the therapeutic agent or fluid flows directly through the lumen 605 to the fluid collection chamber 626. Following completion of the procedure the device 300, 500, 600 is removed from the patient, disconnected from the fluid supply and/or pressure generating device and power source and disposed of.

When the desired treatment site is accessed for an electroporation procedure requiring negative fluid pressure, such as aspiration of excess fluid, the device 300, 500, 600 is connected to a vacuum or aspirating device such as a mechanical pump or hand operated syringe 40. An electric signal having a voltage differential ranging between about less than 1 to 2000 mV/cm$^2$, with a preferable range of less than 5 to 1000 mV/cm$^2$, is sent through the second electrical lead 344, 544, 618 from a power source 354, 554, 620. A recommended pattern of impressing the electric signal is one such as exponential logarithmic wave forms or square wave forms, but is not limited to those. In another embodiment the electrical signal may be pulsed, i.e., periodically turned on and off or varied in intensity. The electric signal for electroporation is preferably applied one or more times. The electric signal flows from the proximal section of the second hollow member 304a, 504a or solid member 602 to the first hollow member 302, 502, or distally down the length of the solid member 602. The electric signal causes an increase in cellular permeability due to the process of forming very small openings (pores) in the plasma membrane, which increases the body's ability to give up fluid. Negative pressure is applied to the first lumen 332, 532 or lumen 605 which extends to the fluid collection chamber 308, 508, 626. A negative pressure potential is created between the fluid collection chamber 308, 508, 626 and the environment immediately outside the device 300, 500, 600 which allows fluid surrounding the outer surface (unnumbered) and region of the semi-permeable membrane 306, 506, 606 to be drawn through the semi-permeable membrane 306, 506, 606 through the opening or openings 314, 514 into the first lumen 332, 532 or directly into the lumen 605. Once in the first lumen 332, 532 or lumen 605 the fluid is proximally transported outside the device 300, 500, 600 where it is disposed of or stored for further analysis. Following completion of the procedure the device 300, 500, 600 is removed from the patient, disconnected from the fluid supply and/or pressure generating device and power source and disposed of.

What is claimed is:

1. A catheter for use in a tissue treatment site, the catheter comprising:
  a. a first conductive member comprising an outer surface, a lumen capable of transporting fluids along a length of the first conductive member, an opening through the first conductive member allowing fluid communication between the lumen and the outer surface of the first conductive member, a proximal insulated portion, and a distal uninsulated portion;
  b. a proximal second conductive member section having an exterior surface comprising an uninsulated distal portion forming a portion of an exterior surface of the catheter and surrounding the insulated portion of the first conductive member; and
  c. a semi-permeable membrane having an exterior surface attached to the first conductive member and extending across the opening to regulate fluid passage through the first conductive member, wherein the exterior surface of the proximal second conductive member and the exterior surface of the semi-permeable membrane are co-planar;
  d. a first conductor in electrical communication with the first conductive member; and
  e. a second conductor in electrical communication with the second conductive member;
  wherein when the catheter is inserted into a patient tissue treatment site, electrical current supplied to one of the first or second conductive members passes from the uninsulated portion of the first or second conductive member, through the patient tissue, and to the uninsulated portion of the other of the first or second conductive member to electroporate the tissue at the tissue treatment site; and,
  wherein the semi-permeable membrane provides the external surface of a fluid collection chamber within the catheter, which in turn permits therapeutic fluid to pass into and through the lumen of the catheter, to the fluid collection chamber, through the semi-permeable membrane, and into the tissue treatment site.

2. The catheter of claim 1 wherein the first conductor and the second conductor are in electrical communication with a power source allowing a controlled electric current to flow between the uninsulated portions of the first conductive member and the second conductive member.

3. The catheter of claim 1 wherein when positive fluid pressure is applied to the lumen of the first conductive member, fluid within the lumen will flow out of the lumen through the semi-permeable membrane.

4. The catheter of claim 1 wherein when neutral or less pressure is applied to the lumen of the first conductive member, fluid external to the catheter is drawn through the semi-permeable membrane and into the lumen.

5. The catheter of claim 1 wherein the catheter is sufficiently rigid and sharp to allow the catheter to be introduced into a patient through a skin of the patient without the use of another device.

6. The catheter of claim 1 wherein the semi-permeable membrane extends distally from the uninsulated distal portion of the proximal second conductive member section, and the uninsulated distal portion of the first conductive member extends distally from the semi-permeable membrane.

7. The catheter of claim 6 further comprising an uninsulated distal second hollow conductive member section surrounding the distal portion of the first conductive member and in electrical communication with the distal portion of the first conductive member.

8. The catheter of claim 7 wherein the proximal second conductive member section is proximal to the semi-permeable membrane and wherein the uninsulated distal second hollow conductive member section is distal to the semi-permeable membrane.

9. The catheter of claim 8 wherein the uninsulated distal portion of the proximal second conductive member section, the semi-permeable membrane, and the uninsulated distal second hollow conductive member section form an exterior surface of the catheter.

10. The catheter of claim 6 wherein when the catheter is inserted into a patient tissue, electrical current supplied to either the uninsulated portion of the first conductive member or the proximal second conductive member section, the electrical current passes through the patient tissue, and to the other or the uninsulated portion of the first conductive member or the proximal second conductive member to electroporate the tissue.

11. The catheter of claim 6 wherein the fluid collection chamber is formed between the outer surface of the first conductive member and the semi-permeable membrane to allow the collection of fluid prior to exiting through the semi-permeable membrane when positive fluid pressure is applied to the lumen.

12. The catheter of claim 6 wherein the fluid collection chamber is formed between the outer surface of the first conductive member and the semi-permeable membrane such that when neutral or less pressure is applied to the lumen, fluid external to the catheter is drawn through the semi-permeable membrane, into the fluid collection chamber, through the opening and into the lumen.

13. A catheter according to claim 1 wherein the catheter is adapted for use in a procedure that comprises first infusing the treatment site with the fluid, followed by then delivering an electric signal in order to electoporate the tissue.

14. A catheter according to claim 1 wherein the catheter is adapted for use in a procedure that comprises simultaneously infusing the treatment site with the fluid and impressing an electric signal in order to electoporate the tissue.

15. A catheter according to claim 1 wherein the therapeutic fluid is delivered to the fluid collection chamber under positive pressure through the catheter lumen.

16. A catheter according to claim 1 wherein an electric signal is impressed upon the tissue having a voltage differential of less than 1 to 2000 mV/cm2.

17. A catheter according to claim 1 wherein the catheter further comprises means for permitting the aspiration of fluid from the tissue site.

* * * * *